United States Patent [19]

Inoue et al.

[11] 3,966,731

[45] June 29, 1976

[54] 2-FLUOROMETHYL-3-o-TOLYL-6-AMINO-4(3H)-QUINAZOLINONE

[75] Inventors: Ichizo Inoue, Ikeda; Toyonari Oine, Nara; Yoshihisa Yamada, Kyoto; Junichi Tani; Ryuichi Ishida, both of Osaka; Takashi Ochiai, Kobe, all of Japan

[73] Assignee: Tanabe Seiyaku Co., Ltd., Osaka, Japan

[22] Filed: Sept. 30, 1974

[21] Appl. No.: 510,577

[30] Foreign Application Priority Data

Oct. 15, 1973 Japan.............................. 48-115512

[52] U.S. Cl................. 260/256.4 Q; 260/251 QA; 260/256.5 R; 260/558 R; 260/558 A; 424/250

[51] Int. Cl.$^2$.................................. C07D 239/91

[58] Field of Search............... 260/256.4 Q, 256.5 R

[56] References Cited

UNITED STATES PATENTS 3,414,573  12/1968  Breuer......................... 260/256.4 Q

FOREIGN PATENTS OR APPLICATIONS 882,430  12/1961  France......................... 260/256.4 Q
947,842  9/1963  France......................... 260/256.4 Q

OTHER PUBLICATIONS

Boehringer Co., "Chemical Abstracts" of Fr. 1,412,615, 1965, p. 5112ff, vol. 64.

Burger, "Medicinal Chemistry," p. 43, 1963.

*Primary Examiner*—Alton D. Rollins
*Assistant Examiner*—David E. Wheeler
*Attorney, Agent, or Firm*—Bierman & Bierman

[57] ABSTRACT

N-(2-amino-5-nitrobenzoyl)-o-toluidine is condensed with fluoroacetic acid or a functional derivative thereof. N-(2-fluoroacetamido-5-nitrobenzoyl)-o-toluidine obtained by said condensation reaction is dehydrated to produce 2-fluoromethyl-3-(o-tolyl)-6-nitro-4(3H)-quinazolinone, which is then subjected to reduction reaction. 2-fluoromethyl-3-(o-tolyl)-6-amino-4(3H)-quinazolinone thus obtained and a pharmaceutically acceptable acid addition salt thereof are useful as central muscle relaxants, minor tranquilizers, anti-convulsants, analgesics and/or anti-inflammatory agents.

2 Claims, No Drawings

2-FLUOROMETHYL-3-O-TOLYL-6-AMINO-4(3H)-QUINAZOLINONE

This invention relates to a novel quinazolinone derivative and a process for preparing same. More particularly, it relates to 2-fluoromethyl-3-(o-tolyl)-6-amino-4(3H)-quinazolinone(hereinafter referred to as "the quinazolinone derivative [I]"). Pharmaceutically acceptable acid addition salts of 2-fluoromethyl-3-(o-tolyl)-6-amino-4(3H)-quinazolinone are also included within the scope of the present invention.

We have now found that the quinazolinone derivative [I] of the present invention and a pharmaceutically acceptable acid addition salt thereof are useful as central muscle relaxants, minor tranquilizers, anti-convulsants, analgesics and/or anti-inflammatory agents. As shown in the following Table 1, the central muscle relaxing activity of the quinazolinone derivative [I] is about 3 to 7 times stronger than that of 2-fluoromethyl-3-(o-tolyl)-4(3H)-quinazolinone. Further, although 2-methyl-3-(o-tolyl)-6-amino-4(3H)-quinazolinone have relatively strong muscle relaxing activity, the quinazolinone derivative [I] of the present invention is apparently about 7 times superior to said known quinazolinone in safety margin(i.e., the potency ratio of the muscle relaxing activity to the acute toxicity).

1972 under the number 48483/1972]. Further, Breuer et al discloses that 2-methyl-3-(o-tolyl)-6-amino-4(3H)-quinazolinone shows a muscle relaxing activity[Arzneimittel Forshung 21(1971), NO. 2, 238–243; c.f., U.S. Pat. No. 3317388]. As compared with these known quinazolinones, however, the quinazolinone derivative [I] is more useful as a central muscle relaxant because of its stronger activity, greater therapeutic index and/or greater safety margin. For example, as shown in Table 1, the muscle relaxing activity of the quinazolinone derivative [I] is about 3 to 7 times stronger than that of 2-fluoromethyl-3-(o-tolyl)-4(3H)-quinazolinone.

Table 1

| Compounds | Muscle relaxing activity $ED_{50}$(mg/kg) | | | Side effect Hypnotic activity $HD_{50}$ (mg/kg) (D) | Acute toxicity $LD_{50}$(mg/kg) (E) | Therapeutic index | | | Safety margin | | |
|---|---|---|---|---|---|---|---|---|---|---|---|
| | (A) | (B) | (C) | | | D/A | D/B | D/C | E/A | E/B | E/C |
| The quinazolinone derivative [I] of the present invention | 20.7 | 19.3 | 22.4 | 53.1 | 528.0 | 2.57 | 2.75 | 2.37 | 25.5 | 27.4 | 23.6 |
| (Prior arts) | | | | | | | | | | | |
| 2-fluoromethyl-3-(o-tolyl)-4(3H)-quinazolinone | 138.4 | 58.9 | 67.5 | 87.3 | 710.0 | 0.63 | 1.48 | 1.29 | 5.1 | 12.1 | 10.5 |
| 2-fluoromethyl-3-(o-tolyl)-6-nitro-4(3H)-quinazolinone | >100 | >100 | >100 | >100 | — | — | — | — | — | — | — |
| 2-methyl-3-(o-tolyl)-6-amino-4(3H)-quinazolinone | 24.0 | 22.5 | 22.5 | 33.7 | 87.5 | 1.40 | 1.49 | 1.49 | 3.7 | 3.9 | 3.9 |
| Mephenesin | 527.3 | 551.2 | 497.8 | 824.1 | 2020.0 | 1.56 | 1.50 | 1.66 | 3.8 | 3.7 | 4.1 |
| Chlormezanone | 207.5 | 156.2 | 221.6 | 385.5 | 1340.1 | 1.86 | 2.47 | 1.74 | 6.5 | 8.6 | 6.1 |

Note:
(A): Activity examined by the traction method. A drug was administered orally to mice. After 10, 20 and 30 minutes of the dosing, the mice were suspended by the forepaws to a metallic wire of 1 mm in diameter. $ED_{50}$ of the drug was estimated from the number of mice which fell out of the wire within 10 seconds.
(B): Activity examined by the inclined plate method. A drug was administered orally to mice. After 15, 30 and 45 minutes of the dosing, the mice were put on the center of a canvas (60 cm in length and 50 cm in width) having been set up with an inclination of 60 degrees. $ED_{50}$ of the drug was estimated from the number of mice which slipped down from the canvas within one minute.
(C): Activity examined by the rotating rod method. A drug was administered orally to mice. After 30 minutes of the dosing, the mice were placed for 2 minutes on rotating rods (3.5 cm in diameter, 14 rpm.). $ED_{50}$ of the drug was estimated from the number of mice which fell out of the rods twice during the test.
(D): A drug was administered orally to mice. The hypnotic activity of the drug was determined by the number of mice which lost righting reflex for more than 20 seconds. $HD_{50}$ of the drug was estimated as the dose which was required to produce the losing of righting reflex in 50 % of the mice.
(E): A drug was administered orally to mice. The 50 % lethal dose ($LD_{50}$) of the drug was estimated from the number of mice which died 72 hours after the dosing.
Therapeutic index and Safety margin: Said index and margin were calculated from the $ED_{50}$, $HD_{50}$ and $LD_{50}$-values shown in Table 1.

about 22 to 29 times stronger than that of Mephenesin [Chemical name: 3-(o-tolyloxy)-1,2-propanediol] and about 8 to 10 times stronger than that of Chlormezanone[Chemical name: 2-(p-chlorophenyl)tetrahydro-3-methyl-4H-1,3-thiazin-4-one 1,1-dioxide]. Moreover, as compared with known muscle relaxants, quinazolinone derivative [I] is characterized by the greater safety because of its lower side effects and/or toxicity. For example, although the known muscle relaxants such as Mephenesin and Chlormezanone show potent hypnotic activity which is one of the typical side effects thereof, the quinazolinone derivative [I] shows relatively less hypnotic activity and is about 2 times superior to Mephenesin and Chlormezanone in the therapeutic index (i.e., the potency ratio of the muscle relaxing activity to the hypnotic activity).

Inoue et al discloses that 2-fluoromethyl-3-(o-tolyl)-4(3H)-quinazolinone and 2-fluoromethyl-3-(o-tolyl)-6-nitro-4(3H)-quinazolinone are useful as hypnotic agents[Japanese patent application No. 81910/1971 laid open to the public without examination on July 9, The quinazolinone derivative [I] of the present invention has potent tranquilizing, anti-convulsive and analgesic activities. For example, as shown in the following Table 2, the anti-cardiazol activity($ED_{50}$) of the quinazolinone derivative which is estimated as the preventive effect against cardiazol-induced convulsive death in mice is about 2 times superior to that of Chlormezanone, and the analgesic activity($ED_{50}$) thereof examined by the acetic acid-writhing method is apparently stronger than that of Chlormezanone. The anti-cardiazol activity of the quinazolinone derivative [I] is also 3.6 and 1.1 times superior to those of 2-fluoromethyl-3-(o-tolyl)-4(3H)-quinazolinone and 2-methyl-3-(o-tolyl)-6-amino-4(3H)-quinazolinone, respectively. Additionally, the quinazolinone derivative [I] has a potent anti-inflammatory activity. For example, as shown in Table 2, the quinazolinone derivative [I] prevents carageenin-induced edema by 28% when administered orally to rats at the dose of 30 mg/kg. On the other hand, when examined under the same condition as above, 200 mg of Mefenamic acid[Chemical name: N-(2,3-xylyl)anthranilic acid] are required to produce 25% decrease in said carageenin-induced edema.

Table 2

| Compounds | Anti-cardiazol activity $ED_{50}$ (mg/kg) | Analgesic activity $ED_{50}$ (mg/kg) | Anti-inflammatory activity |
|---|---|---|---|
| The quinazolinone derivative [I] of the present invention | 15.7 | 11.8 | 28 % |
| (Prior arts) 2-fluoromethyl-3-(o-tolyl)-4(3H)-quinazolinone | 56.1 | 42.1 | — |
| 2-methyl-3-(o-tolyl)-6-amino-4(3H)-quinazolinone | 16.9 | 10.0 | — |
| Mephenesin | 599.8 | — | — |
| Chlormezanone | 28.8 | 257.6 | — |

Note:
Anti-cardiazol activity. A drug was administered orally to mice. After 30 minutes of the dosing, 125 mg of cardiazol were injected subcutaneously to the mice. $ED_{50}$ of the drug was estimated from the number of mice which were protected from cardiazol-induced convulsive death 60 minutes after injection of cardiazol.
Analgesic activity. One % acetic acid solution was injected intraperitoneally to mice at the dose of 10 mg/kg after oral administration of a drug, and the number of writhings per mouse was counted for 5 minutes starting at 10 minutes after injection of acetic acid. $ED_{50}$ of the drug was estimated as the dose which would produce 50 % reduction in acetic acid-induced writhings.
Anti-inflammatory activity. A drug was administered orally to rats at the dose of 30 mg/kg. To the control group was administered orally a physiological saline solution. After one hour, one % caragenin solution was injected subcutaneously to the rats through planta of hind legs at the dose of 0.5 ml/rat. Then, the volume of the hind legs in the control and medicated groups were measured at 3 hours after injection of caragenin, and the preventive effect (%) of the drug against caragenin-induced edema was calculated therefrom.

The quinazolinone derivative [I] of the present invention can be used for pharmaceutical use either as the free base or as its salt. Pharmaceutically acceptable acid addition salts of the quinazolinone derivative [I] include, for example, hydrochloride, hydrobromide, perchlorate, nitrate, sulfate, phosphate, methanesulfonate, ethanesulfonate, benzenesulfonate, p-toluenesulfonate and sulfanilate. The quinazolinone derivative [I] may be used in the form of a pharmaceutical preparation for enteral or parenteral administration. The daily dose of the quinazolinone derivative [I] suitable for pharmaceutical use may be within the range of 1 to 200 mg/kg, especially 3 to 100 mg/kg. The most preferred daily dose of the quinazolinone derivative [I] suitable for enteral administration may be within the range of 5 to 50 mg/kg. Moreover, the quinazolinone derivative [I] of the present invention may be used in conjunction or admixture with a pharmaceutical excipient which is suitable for enteral or parenteral administration. The excipient selected should be the one which does not react with the quinazolinone derivative [I]. Suitable excipients include, for example, gelatin, lactose, glucose, sodium chloride, starch, magnesium stearate, talcum, vegetable oil, benzyl alcohol and gums. The pharmaceutical preparation may be a solid dosage form such as a tablet, a coated tablet, a pill or a capsule, or a liquid dosage form such as a solution, a suspension or an emulsion. The pharmaceutical preparation may be sterilized and/or may contain auxiliaries such as preserving, stabilizing, wetting or emulsifying agents.

According to the present invention, the quinazolinone derivative [I] can be prepared by the steps of condensing N-(2-amino-5-nitrobenzoyl)-o-toluidine [II] with fluoroacetic acid [III] or a functional derivative thereof, dehydrating the resultant N-(2-fluoroacetamido-5-nitrobenzoyl)-o-toluidine [IV] to produce 2-fluoromethyl-3-(o-tolyl)-6-nitro-4(3H)-quinazolinone [V], and then reducing said quinazolinone [V].

The above-mentioned reactions of the present invention are shown by the following scheme:

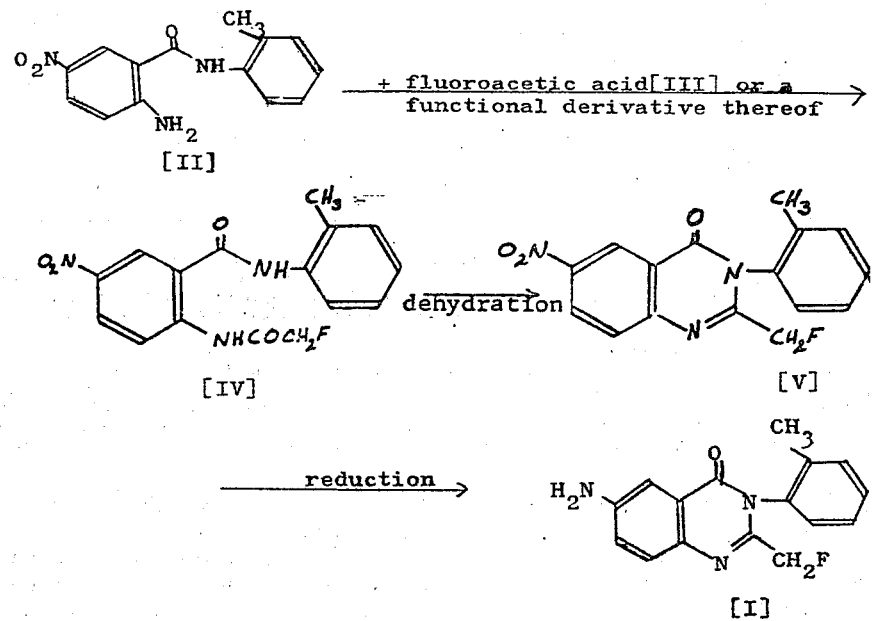

The condensation reaction of N-(2-amino-5-nitrobenzoyl)-o-toluidine [II] with fluoroacetic acid [III] or a functional derivative thereof can be accomplished by conventional manner. For example, the condensation reaction of the compound [II] with fluoroacetic acid [III] is carried out in the presence of a dehydrating agent in a solvent. N,N'-dicyclohexylcabodiimide, N,N'-carbonyl-imidazol and the like are preferably employed as the dehydrating agent. Dimethylformamide and dimethylacetamide are suitable as the reaction solvent. It is preferred to carry out the reaction at a temperature of 15° to 100°C. Alternatively, the condensation reaction of the compound [II] with the functional derivative of fluoroacetic acid [III] is carried out in the presence of an acid acceptor in a solvent. Organic bases such as pyridine and triethylamine, and inorganic bases such as alkali metal carbonate(e.g., sodium carbonate, or potassium carbonate) are employed as the acid acceptor. Tetrahydrofuran and dioxane are suitable as the reaction solvent. Preferred examples of the functional derivative of fluoroacetic acid include the corresponding acid anhydride and acid halide(e.g., chloride, bromide). When fluoroacetic acid anhydride is employed, it is preferred to carry out the reaction at a temperature of 15° to 100°C. On the other hand, when fluoroacetyl halide is employed, it is preferred to carry out the reaction at a temperature of 0° to 50°C.

The subsequent dehydration reaction can be conducted by treating N-(2-fluoroacetamido-5-nitrobenzoyl)-o-toluidine [IV] with a dehydrating agent. Suitable examples of the dehydrating agent include acetic acid anhydride, polyphosphoric acid and alkyl polyphosphate. The reaction is preferably carried out at a temperature of 50° to 150°C.

The reduction reaction of 2-fluoromethyl-3-(o-tolyl)-6-nitro-4(3H)-quinazolinone [V] can be readily accomplished. For example, the quinazolinone derivative [I] is prepared by catalytic hydrogenation of 2-fluoromethyl-3-(o-tolyl)-6-nitro-4(3H)-quinazolinone. Said catalytic hydrogenation is carried out in the presence of a catalyst in hydrogen atmosphere. Examples of the catalyst include palladium-carbon, Raney-nickel and so forth. The reaction is preferably carried out at a pressure of atmospheric pressure to 100 lb and at a temperature of 10° to 100°C. Tetrahydrofuran, acetic acid, 10% hydrochloric acid and 10% hydrobromic acid are suitable as the reaction solvent. Alternatively, the quinazolinone derivative [I] of the invention is prepared by treating 2-fluoromethyl-3-(o-tolyl)-6-nitro-4(3H)-quinazolinone with a reducing agent such as a multivalent metal halide(e.g., stannous chloride). This reduction reaction is preferably carried out in the presence of a concentrated hydrohalic acid (e.g., concentrated hydrochloric acid) at a temperature of 0° to 50°C. Methanol, ethanol, isopropanol, ether and tetrahydrofuran are suitable as the reaction solvent.

Practical and presently-preferred embodiments of the present invention are illustratively shown in the following Examples.

EXAMPLE 1

14.4 g(0.053 mol) of N-(2-amino-5-nitrobenzoyl)-o-toluidine and 6.3 g(0.08 mol) of pyridine are dissolved in 300 ml of tetrahydrofuran. 12.2 g(0.126 mol) of fluoroacetyl chloride are added to the solution for 10 minutes under ice-cooling. The solution is stirred at the same temperature for 30 minutes and then at room temperature for 2.5 hours. The reaction solution is allowed to stand at room temperature overnight. The crystalline precipitate is collected by filtration, washed with water and then dried. 16.4 g of N-(2-fluoroacetamido-5-nitrobenzoyl)-o-toluidine are obtained.

Yield: 93.7 %; M.p. 238°–239°C.

Infrared absorption spectrum: $\nu_{max.}^{liquid\ paraffin}$(cm$^{-1}$): 3250, 1690, 1640, 1610, 1580.

Nuclear magnetic resonance spectrum: $\delta$ in DMSO-$d_6$ : 2.26(s, 3H), 5.08(d, 2H, J = 47 HZ), 7.27(s,4H), 8.35–8.95(m, 3H)

16.5 g(0.05 mol) of N-(2-fluoroacetamido-5-nitrobenzoyl)-o-toluidine and 25.5 g(0.25 mol) of acetic acid anhydride are dissolved in 250 ml of glacial acetic acid. The solution is refluxed for 2 hours under heating. Then, the reaction solution is evaporated to remove solvent. The residue thus obtained is poured into ice-water, and the aqueous mixture is adjusted to pH 9 with potassium carbonate. The crystalline precipitate is collected by filtration. 15.5 g of 2-fluoromethyl-3-(o-tolyl)-6-nitro-4(3H)-quinazolinone are obtained.

Yield: 98.7 %; M.p. 155°–158°C(recrystallized from ethanol).

Infrared absorption spectrum: $\nu_{max.}^{liquid\ paraffin}$(cm$^{-1}$): 1705, 1610, 1588, Nuclear magnetic resonance spectrum: $\delta$ in CDCl$_3$: 2.14(s, 3H), 4.96(d, 2H, J, = 47 HZ), 7.05–9.20(m, 7H)

A mixture of 2.0 g(0.064 mol) of 2-fluoromethyl-3-(o-tolyl)-6-nitro-4(3H)-quinazolinone, 0.2 g of 5% palladium-carbon and 100 ml of acetic acid is shaken for 30 minutes in hydrogen gas. The initial pressure of hydrogen gas is adjusted to 46 lb and the mixture is heated with an infrared lamp during the reaction. After 30 minutes of said reaction, the pressure of hydrogen gas decreases to 6 lb. After the mixture is cooled, said mixture is filtered to remove the catalyst. The filtrate is evaporated to remove acetic acid, and the residue is dissolved in chloroform. The chloroform solution is washed with 5% aqueous sodium hydroxide and water, successively. Then, the solution is dried and evaporated to remove solvent. The oily residue thus obtained is dissolved in 2 ml of chloroform, and the chloroform solution is passed through a column of 200 g of silica gel. The silical gel column is eluted with ethyl acetate-benzene( 1 : 1). Then, the eluate is evaporated to remove solvent. The crude crystal obtained is washed with isopropylether and recrystallized from isopropanol. 0.95 g of 2-fluoromethyl-3-(o-tolyl)-6-amino-4(3H)-quinazolinone is obtained.

Yield: 52.5 %; M.p. 195°–196°C.

Infrared absorption spectrum: $\nu_{max.}^{liquid\ paraffin}$(cm$^{-1}$): 3470, 3370, 1670, 1630

Nuclear magnetic resonance spectrum: $\delta$ in CDCl$_3$ : 2.11(s, 3H), 3.96(s, 2H), 4.91(d, 2H, J = 47 HZ), 6.95 - 7.70(m, 7H)

Hydrochloride: M.p. 205°–208°C(decomp.)

Infrared absorption spectrum: $\nu_{max.}^{liquid\ paraffin}$(cm$^{-1}$): 2400, 1668, 1617, 1488 p-Toluenesulfonate : M.p. 125°–128°C(decomp.)

Infrared absorption spectrum: $\nu_{max.}^{liquid\ paraffin}$(cm$^{-1}$): 3350, 1690, 1613, 1490

EXAMPLE 2

1.36 g of N-(2-amino-5-nitrobenzoyl)-o-toluidine, 0.79 g of pyridine and 0.76 g of fluoroacetic acid anhydride are added to 25 ml of tetrahydrofuran, and the mixture is refluxed for 6 hours under heating. The reaction mixture is evaporated under reduced pressure to remove tetrahydrofuran. Water is added to the residue thus obtained, and the crystalline precipitate is collected by filtration. The crystal is washed with isopropanol and chloroform, and then dried. 1.15 g of N-(2-fluoroacetamido-5-nitrobenzoyl)-o-toluidine are obtained.

Yield: 70 %; M.p. 235°–238°C.

N-(2-fluoroacetamido-5-nitrobenzoyl)-o-toluidine is treated in the same manner as described in Example 1, whereby 2-fluoromethyl-3-(o-tolyl)-6-nitro-4(3H)-quinazolinone is obtained.

A mixture of 2.0 g of 2-fluoromethyl-3-(o-tolyl)-6-nitro-4(3H)-quinazolinone, 0.2 g of 5% palladium-carbon and 100 ml of 10% hydrochloric acid is shaken at 40°C for 1.5 hours in hydrogen gas. The initial pressure of hydrogen gas is adjusted to 48 lb. After said reaction, the mixture is cooled and filtered to remove the catalyst. The filtrate is neutralized with sodium bicarbonate, and the precipitate is extracted with benzene. The benzene solution is dried and then evaporated to remove solvent. The residue thus obtained is recrystallized from isopropanol. 1.3 g of 2-fluoromethyl-3-(o-tolyl)-6-amino-4(3H)-quinazolinone are obtained.

Yield: 72 %; M.p. 195°–196°C.

EXAMPLE 3

2.5 g of 2-fluoromethyl-3-(o-tolyl)-6-nitro-4(3H)-quinazolinone are suspended in 40 ml of methanol, and a solution of 6.0 g of stannous chloride in 6.0 ml of concentrated hydrochloric acid is added dropwise thereto at 5° to 10°C for 15 minutes. The mixture is stirred at the same temperature for 15 minutes and then at room temperature for 2.5 hours. After the reaction, the mixture becomes a clear solution. The solution thus obtained is decolorized with 0.25 g of activated carbon. 200 ml of water and 100 ml of chloroform are added to the solution. Then, the solution is neutralized with sodium bicarbonate, stirred and filtered to remove insoluble materials. The chloroform layer is separated, dried and then concentrated to dryness. The residue thus obtained is crystallized with 15 ml of isopropanol, and the crystalline precipitate is collected by filtration. 1.9 g of 2-fluoromethyl-3-(o-tolyl)-6-amino-4(3H)-quinazolinone are obtained.

Yield: 84%; M.p. 195°–196°C.

What we claim is:

1. 2-fluoromethyl-3-(o-tolyl)-6-amino-4(3H)-quinazolinone or a pharmaceutically acceptable acid addition salt thereof.

2. The compound as claimed in claim 1, wherein said pharmaceutically acceptable acid addition salt is selected from the group consisting of hydrochloride, hydrobromide, perchlorate, nitrate, sulfate, phosphate, methanesulfonate, ethanesulfonate, benzenesulfonate, p-toluenesulfonate and sulfanilate.

* * * * *